US00RE46583E

(19) United States
(12) Reissued Patent
Dietrich et al.

(10) Patent Number: US RE46,583 E
(45) Date of Reissued Patent: Oct. 24, 2017

(54) VACCINES COMPRISING TB10.4

(71) Applicant: Statens Serum Institut, Copenhagen S (DK)

(72) Inventors: Jes Dietrich, Copenhagen (DK); Claus Aagaard, Copenhagen S (DK); Peter Andersen, Brønshøj (DK)

(73) Assignee: Statens Serum Institut, Copenhagen (DK)

(21) Appl. No.: 14/851,672

(22) Filed: Sep. 11, 2015

Related U.S. Patent Documents

Reissue of:
(64) Patent No.: 8,557,258
Issued: Oct. 15, 2013
Appl. No.: 13/221,211
Filed: Aug. 30, 2011

U.S. Applications:
(62) Division of application No. 12/500,881, filed on Jul. 10, 2009, now abandoned.

(60) Provisional application No. 61/085,973, filed on Aug. 4, 2008.

(30) Foreign Application Priority Data

Jul. 15, 2008 (DK) ..... 2008 00997

(51) Int. Cl.
*A61K 39/00* (2006.01)
*A61K 39/02* (2006.01)
*A61K 39/04* (2006.01)
*A61K 39/38* (2006.01)

(52) U.S. Cl.
CPC ..... *A61K 39/04* (2013.01); *A61K 2039/545* (2013.01); *A61K 2039/55516* (2013.01); *A61K 2039/55561* (2013.01)

(58) Field of Classification Search
CPC ..... A61K 39/04; A61K 2039/545
USPC ..... 424/248.1, 190.1, 184.1, 234.1, 236.1
See application file for complete search history.

(56) References Cited

U.S. PATENT DOCUMENTS

| | | | | |
|---|---|---|---|---|
| 5,108,745 | A | 4/1992 | Horwitz | |
| 5,955,077 | A | 9/1999 | Andersen et al. | |
| 6,436,409 | B1 | 8/2002 | Gicquel et al. | |
| 6,641,814 | B1 | 11/2003 | Andersen et al. | |
| 6,649,170 | B1 | 11/2003 | Lindblad et al. | |
| 6,806,355 | B2 | 10/2004 | Joergensen et al. | |
| 6,944,383 | B1 | 9/2005 | Herzog | |
| 6,982,085 | B2 | 1/2006 | Andersen et al. | |
| 7,037,510 | B2 | 5/2006 | Andersen et al. | |
| 7,666,656 | B2 | 2/2010 | Sun et al. | |
| 7,838,013 | B2 | 11/2010 | Andersen et al. | |
| 7,838,018 | B2 | 11/2010 | Lindblad et al. | |
| 7,867,502 | B1 | 1/2011 | Andersen et al. | |
| 7,968,105 | B2 | 6/2011 | Aagaard et al. | |
| 8,323,660 | B2 * | 12/2012 | Meinke et al. | 424/190.1 |
| 8,361,476 | B2 * | 1/2013 | Fritz et al. | 424/184.1 |
| 2004/0057963 | A1 | 3/2004 | Andersen et al. | |
| 2005/0191308 | A1 | 9/2005 | Lindblad et al. | |
| 2006/0008519 | A1 | 1/2006 | Davidsen et al. | |
| 2008/0008724 | A1 | 1/2008 | Aagaard et al. | |
| 2008/0299151 | A1 | 12/2008 | Fomsgaard et al. | |
| 2009/0186048 | A1 | 7/2009 | Aagaard et al. | |
| 2010/0015171 | A1 | 1/2010 | Dietrich et al. | |
| 2010/0297170 | A1 | 11/2010 | Buschle et al. | |
| 2010/0310585 | A1 | 12/2010 | Agger et al. | |
| 2011/0020384 | A1 | 1/2011 | Andersen et al. | |
| 2011/0250237 | A1 * | 10/2011 | O'Hagan et al. | 424/400 |
| 2012/0014980 | A1 * | 1/2012 | Dietrich et al. | 424/185.1 |

FOREIGN PATENT DOCUMENTS

| | | |
|---|---|---|
| WO | WO 01/23388 | 4/2001 |
| WO | WO 01/35317 | 5/2001 |
| WO | WO 01/79274 | 10/2001 |
| WO | WO 03/004520 | 1/2003 |
| WO | WO 2004/006952 | 1/2004 |
| WO | WO 2005/061534 | 7/2005 |
| WO | WO 2006/053871 | 5/2006 |
| WO | WO 2006/136162 | 12/2006 |
| WO | WO 2008/000261 | 1/2008 |
| WO | WO 2009/003474 | 1/2009 |
| WO | WO 2010/006607 | 1/2010 |

(Continued)

OTHER PUBLICATIONS

Vaccine. 33(2015) 3592-3599.*
Aagaard, "Quality and vaccine efficacy of CD4+ T cell responses directed to dominant and subdominant epitopes in ESAT-6 from *Mycobacterium tuberculosis*", The Journal of Immunology, 183(4):2659-2668 (Aug. 15, 2009; Epub Jul. 20, 2009).
Billescov, "The HyVac4 Subunit Vaccine Efficiently Boosts BCG-Primed Anti-Mycobacterial Protective Immunity", PLoS One, 7(6):e39909 (10 pp.) (Jun. 29, 2012).
Leroux-Roels, "Improved CD4+ T cell responses to *Mycobacterium tuberculosis* in PPD-negative adults by M72/AS01 as compared to the M72/AS02 and Mtb72F/AS02 tuberculosis candidate vaccine formulations: A randomized trial", Vaccine 31:2196-2206 (May 27, 2012).

(Continued)

*Primary Examiner* — Shri Ponnaluri
(74) *Attorney, Agent, or Firm* — Howson & Howson LLP

(57) ABSTRACT

Vaccination with the combination of Ag85B-TB10.4 and IC31® adjuvant generated a high amount of polyfunctional $CD4^{+}$T cells expressing high levels of IFN-γ, TNF-α, and IL-2. This in turn led to significant protection against infection with M. tuberculosis in the mouse aerosol challenge model of tuberculosis. Both the immunogenicity of the vaccine and its ability to protect against TB infection was highly dependent on the antigen dose. Thus, whereas the standard antigen dose of 5 μg, as well as 15 μg, did not induce significant protection against M. tuberculosis, reducing the dose to 0.5 μg increased both the immunogenicity of the vaccine as well as its protective efficacy to a level comparable to that observed in BCG vaccinated mice. Thus, the IC31® adjuvant, with the specified antigen dose, can induce a strong protective Th1 response against M. tuberculosis.

20 Claims, 3 Drawing Sheets

(56) References Cited

FOREIGN PATENT DOCUMENTS

| | | |
|---|---|---|
| WO | WO 2010/034974 | 1/2010 |
| WO | WO 2010/034974 | 4/2010 |

OTHER PUBLICATIONS

Spertini, "The candidate tuberculosis vaccine Mtb72F/AS02 in PPD positive adults: A randomized controlled phase I/II study", tuberculosis 93:179-188 (Mar. 2013, e-pub Dec. 5, 2012).
Van Dissel, "A novel liposomal adjuvant system, CAF01, promotes long-lived *Mycobacterium tuberculosis*-specific T-cell responses in human", Vaccine, 32:7098-7107 (Oct. 30, 2014).
Van Dissel, "Ag85B-ESAT-6 adjuvanted with IC31® promotes strong and long-lived *Mycobacterium tuberculosis* specific T cell responses in naïve human volunteers", Vaccine, 28:3571-3581 (Mar. 2010).
Van Dissel, "Ag85B-ESAT-6 adjuvanted with IC31® promotes strong and long-lived *Mycobacterium tuberculosis* specific T cell responses in volunteers with previous BCG vaccination or tuberculosis infection", Vaccine, 29:2100-2109 (Jan. 2011).
Wu, et al., Distinct Lineages of $T_H$I Cells Have Differential Capacities for Memory Cell Generation in Vivo, Nature Immunology, 3(9): 852-858 (Sep. 2002) Epublication: Aug. 12, 2002.
Orme, Microbes and Infection, 2005, 7:905-910.*
van Dissel et al, Vaccine, 2011, 29:2100-2109.*
Yu et al, Scandinavian J. Immunology, 2011, 73/6:568-576.*
Andersen, TRENDS in Immunology, Mar. 2001, 22/3:160-.*
Christensen et al, Journal of Liposome Research, 2009; 19(1): 2-11.*
Henriksen-Lacey et al, vol. 8, No. 1, 153-161 Molecular Pharmaceutics.*
Langermans et al, Vaccine 23 (2005) 2740-2750.*
Mohammed et al,European Journal of Pharmaceutics and Biopharmaceutics 76 (2010) 404-412.*
Ottenhoff et al,Human Vaccines 6:12, 1007-1015; Dec. 2010.*
Takatsu et al, International Immunopharmacology 3 (2003) 783-800.*
Intercell::Adjuvant IC31, printed from Internet, Mar. 26, 2012, 1 page.*
Lingnau et al, Expert Rev. Vaccines, 2007, 6/5:741-746.*
Schellack et al, Vaccine, 2006, 24:5461-5472.*
Kreig (BioDrugs 1998, 5:341-346).*
Yamamoto et al 1994 (Antisense Research and Development, 1994, 4:119-122).*
Agarwal et al. (Trends in Mol. Med., 2002; 8:114-121).*
Hartmann et al. (J. Immunology, 2000; 164:1617-1624).*
Weiner (J. Leukocyte Biology, 68:456-463, 2000).*
Agarwal et al, Molecular Med, Today, 6:72-81, 2000.*
Goodman, FDA (US Food and Drug Administration). Dec. 2-3, 2008.*
Nagy, Workshop on Adjuvants and Innate Immunity, Brussels, Jul. 2, 2009.*
Nagy, Intercell Smart Vaccines (IC31—A novel adjuvant for vaccine development), Dec. 3, 2007.*
Olafsdottir et al, Scandinavian Journal of Immunology, 2009, 69, 194-202.*
Aagaard, "Protection and polyfunctional T cells induced by Ag85B-TB10.4/IC31 against *Mycobacterium tuberculosis* is highly dependent on the antigen dose", PLOS One, 4(6):e5930 (Jun. 16, 2009).
Aagaard, "Quality and vaccine efficacy of CD4+T cell responses directed to dominant and subdominant epitopes in ESAT-6 from *Mycobacterium tuberculosis*", The Journal of Immunology, 183(4):2659-2668 (Aug. 15, 2009; Epub Jul. 20, 2009).
Aagaard, "TB vaccines: current status and future perspectives", Immunology & Cell Biology, 87(4):279-286. (May-Jun. 2009; Epub Apr. 7, 2009).
Agger, "Protective immunity to tuberculosis with Ag85B-ESAT-6 in a synthetic cationic adjuvant system IC31", Vaccine, 24(26):5452-5460 (Jun. 2006; Epub Apr. 17, 2006).
Andersen, "Proteins Released from *Mycobacterium tuberculosis* during Growth", Infection and Immunity, 59(6):1905-1910 (Jun. 1991).
Andersen, "Simultaneous electroelution of whole SDS-polyacrylamide gels for the direct cellular analysis of complex protein mixtures", The Journal of Immunology Methods, 161(1):29-39 (May 5, 1993).
Bentrup, Mycobacterial Persistence: Adaptation to a Changing Environment, Trends in Microbiology, 9(12):597-605 (Dec. 2001).
Betts, "Evaluation of a nutrient starvation model of *Mycobacterium tuberculosis* persistence by gene and protein expression profiling", Molecular Microbiology, 43(3):717-731 (Feb. 2002).
Boon, "Proteins of *Mycobacterium bovis* BCG induced in the Wayne dormancy model", Journal of Bacteriology, 183(8):2672-2676 (Apr. 2001).
Brandt, "ESAT-6 Subunit Vaccination against *Mycobacterium tuberculosis*", Infection and Immunity, 68(2):791-795 (Feb. 2000).
Brandt, "Failure of the *Mycobacterium bovis* BCG vaccine: some species of environmental *mycobacteria* block multiplication of BCG and induction of protective immunity to tuberculosis", Infection & Immunity, 70(2):672-678 (Feb. 2002).
Brandt, "The protective effect of the *Mycobacterium bovis* BCG vaccine is increased by coadministration with the *Mycobacterium tuberculosis* 72-kilodalton fusion polyprotein Mtb72F in *M. tuberculosis*-infected guinea pigs", Infection and Immunity, 72(11):6622-6632 (Nov. 2004).
Brock, "Specific T-cell epitopes for immunoassay-based diagnosis of *Mycobacterium tuberculosis* infection", Journal of Clinical Microbiology, 42(6):2379-2387 (Jun. 2004).
Brooks, "Boosting Vaccine for Tuberculosis", Infection and Immunity, 69(4):2714-2717 (Apr. 2001).
Christensen, et al., Liposome-based cationic adjuvant formulations (CAF): Past, present, and future, J. Liposome Research, 2009, 19/1:2-11.
Colditz, "Efficacy of BCG Vaccine in the Prevention of Tuberculosis", The Journal of the American Medical Association, 271(9):698-702 (Mar. 2, 1994).
Cole, "Deciphering the biology of *Mycobacterium tuberculosis* from the complete genome sequence", Nature, 393(6685)537-544 (Jun. 11, 1998).
Cote-Sierra, "A New Membrane-bound OprI lipoprotein Expression Vector High Production of Heterologous Fusion Proteins in Gram (–) Bacteria and the Implications for Oral Vaccination", Gene, 221:25-34 (Aug. 10, 1998).
Darrah, "Multifunctional TH1 cells define a correlate of vaccine-mediated protection against *Leishmania major*", Nature Medicine, 13(7):843-850 (Jul. 2007; Epub: Jun. 10, 2007).
Dietrich, "Exchanging ESAT6 with TB10.4 in an Ag85B fusion molecule-based tuberculosis subunit vaccine: efficient protection and ESAT6-based sensitive monitoring of vaccine efficacy" The Journal of Immunology, 174(10):6332-6339 (May 15, 2005).
Dietrich, "Mucosal administration of Ag85B-ESAT-6 protects against infection with *Mycobacterium tuberculosis* and boosts prior bacillus Calmette-Guerin immunity", The Journal of Immunology, 177(9):6353-6360 (Nov. 1, 2006).
Doherty, "Immune Responses to the *Mycobacterium tuberculosis*-Specific Antigen ESAT-6 Signal Subclinical Infection among Contacts of Tuberculosis Patients", Journal of Clinical Microbiology, 40(2):704-706 (Feb. 2002).
Duffy, et al., Immunological Memory Transferred with CD4 T Cells Specific for Tuberculosis Antigens Ag85B-TB10.4: Persisting Antigen Enhances Protection, PLoS One, Dec. 14, 2009, 4/12:e8272. 8 pgs.
Elvang, "CD4 and CD8 T cell responses to the *M. tuberculosis* Ag85B-TB10.4 promoted by adjuvanted subunit, adenovector or heterologous prime boost vaccination", PLOS One, 4(4):e5139 (Apr. 2009; Epub: Apr. 9, 2009).
Florczyk, "Identification and Characterization of Mycobacterial Proteins Differentially Expressed under Standing and Shaking Culture Conditions, Including Rv2623 from a Novel Class of Putative ATP-Binding Proteins", Infection and Immunity, 69(9):5777-5785, (Sep. 2001).

(56) References Cited

OTHER PUBLICATIONS

Gosselin, "Enhanced Antigen Presentation Using Human Fc(Receptor (Monocyte/Macrophage)-Specific Immunogens", The Journal of Immunology, 149(11):3477-3481 (Dec. 1, 1992).
Hall, "Characterisation of a live *Salmonella* vaccine stably expressing the *Mycobacterium tuberculosis* Ag85B-ESAT6 fusion protein", Vaccine, (Sep. 12, 2009 [Epub ahead of print]).
Harboe, "B-Cell Epitopes and Quantification of the ESAT-6 Protein of *Mycobacterium tuberculosis*", Infection and Immunity, 66(2):717-723 (Feb. 1998).
Hoang, "Distinct differences in the expansion and phenotype of TB10.4 specific CD8 and CD4 T cells after infection with *Mycobacterium tuberculosis*", PLOS One, 16;4(6):e5928 (Jun. 16, 2009).
Horwitz, "Recombinant bacillus calmette-guerin (BCG) vaccines expressing the *Mycobacterium tuberculosis* 30-kDa major secretory protein induce greater protective immunity against tuberculosis than conventional BCG vaccines in a highly susceptible animal model", Proceedings of the National Academy of Sciences, 97(25):13853-13858 (Dec. 5, 2000).
Intercell AG, Statens Serum Institut (SSI), Intercell (ICLL), and Aeras Global Tuberculosis Vaccine Foundation (Aeras) announc . . . , ISIN AT0000612601 Permanent Information Release, Dec. 4, 2007 (retrieved from internet on Feb. 23, 2011).
Kaufmann, et al., New vaccines for tuberculosis, Lancet, 2010, 375:2110-2119.
Kilgus, "Analysis of the Permissive Association of a Malaria T Cell Epitope with DR Molecules", The Journal of Immunology, 146(1):307-315 (Jan. 1, 1991).
Kohler, "Continuous Cultures of Fused Cells Secreting Antibody of Predefined Specificity", Nature, 256(5517):495-497 (Aug. 7, 1975).
Lalvani, "Rapid detection of *Mycobacterium tuberculosis* infection by enumeration of antigen-specific T cells", American Journal of Respiratory and Critical Care Medicine, 163(4):824-828 (Mar. 2001).
Leroux-Roels, "Safety and immunogenicity of the Mtb72f/AS02A tuberculosis vaccine in PPD-negative Belgian adults", Medicine and Health in the Tropics. Marseille, France, (Abstract O-036) (Sep. 11-15, 2005).
Leyten, "Human T-cell responses to 25 novel antigens encoded by genes of the dormancy regulon of *Mycobacterium tuberculosis*", Microbes and Infection, Elsevier, Paris, FR, 8(8):2052-2060 (Jul. 2006; Epub: Jun. 13, 2006).
Lowrie, "Therapy of Tuberculosis in Mice by DNA Vaccination", Nature, 400:269-271 (Jul. 15, 1999).
Lustig, "Humoral and Cellular Responses to Native Antigen Following Oral and Parenteral Immunization with Lipid-Conjugated Bovine Serum Albumin", Cellular Immunology, 24:164-172 (Jun. 1, 1976).
Ly, et al., Tuberculosis: vaccines in the pipeline, Expert Rev. Vaccines, 2008, 7/5: 635-650.
Lyashchenko, "A multi-antigen print immunoassay for the development of serological diagnosis of infectious diseases", The Journal of Immunological Methods, 242(1-2):91-100 (Aug. 28, 2000).
Manganelli, "The *Mycobacterium tuberculosis* ECF Sigma Factor FE: Role in Global Gene Expression and Survival in Macrophages", Molecular Microbiology, 41(2):423-437 (May 2001).
McCafferty, "Phage Antibodies: Filamentous Phage Displaying Antibody Variable Domains", Nature, 348:552-554 (Dec. 6, 1990).
McShane, "Recombinant modified vaccinia virus Ankara expressing antigen 85A boosts BCG-primed and naturally acquired antimycobacterial immunity in humans", Nature Medicine, 10(11):1240-1244 (Nov. 2004; Epub: Oct. 24, 2004).
Merrifield, "Solid Phase Peptide Synthesis. I. The Synthesis of a Tetrapeptide", The Journal of the American Chemical Society, 85(14):2149-2154 (Jul. 20, 1963).
Monahan, "Differential Expression of Mycobacterial Proteins Following Phagocytosis by Macrophages", Microbiology, 147(Part 2):459-471 (Feb. 2001).
Mowat, "Immune-Stimulating Complexes Containing Quil A and Protein Antigen Prime Class I MHC-restricted T Lymphocytes In Vivo and are Immunogenic by the Oral Route", Immunology, 72(3):317-322 (Mar. 1991).
Nagai, "Isolation and Partial Characterization of Major Protein Antigens in the Culture Fluid of *Mycobacterium tuberculosis*", Infection and Immunity, 59(1):372-382 (Jan. 1991).
Olsen, "Efficient protection against *Mycobacterium tuberculosis* by vaccination with a single subdominant epitope from the ESAT-6 antigen", The European Journal of Immunology, 30(6):1724-1732 (Jun. 2000).
Olsen, "Protection of mice with a tuberculosis subunit vaccine based on a fusion protein of antigen 85B and ESAT-6", Infection and Immunity, 69(5):2773-2778 (May 2001).
Orme, The use of animal models to guide rational vaccine design, Microbes and Infection, 2005, 7:905-910.
Pearson, "Improved Tools for Biological Sequence Comparison", Proceedings of the National Academy of Sciences, 85:2444-2448 (Apr. 1988).
Pollock, "Assessment of defined antigens for the diagnosis of bovine tuberculosis in skin test-reactor cattle", The Veterinary Record, 146(23):659-665 (Jun. 23, 2000).
Ravn, "Human T Cell Responses to the ESAT-6 Antigen from *Mycobacterium tuberculosis*", The Journal of Infectious Diseases, 179(3):637-645 (Mar. 1999).
Rolph, "Recombinant Viruses as Vaccines and Immunological Tools", Current Opinion in Immunology, 9(4):517-524 (Aug. 1997).
Rosenkrands, "Hypoxic Response of *Mycobacterium tuberculosis* Studied by Metabolic Labeling and Proteome Analysis of Cellular and Extracellular Proteins", Journal of Bacteriology, 184(13):3485-3491 (Jul. 2002).
Rosenkrands, "Identification an Characterization of a 29-Kilodalton Protein from *Mycobacterium tuberculosis* Culture Filtrate Recognized by Mouse Memory Effector Cells", Infection and Immunity, 66(6):2728-2735 (Jun. 1998).
Sable, et al., Multicomponent antituberculosis subunit vaccine based on immunodominant . . . , Vaccine, 2005, 23:4175-4184.
Sable, et al., Tuberculosis subunit vaccine development: Impact of physiochemical properties of *mycobacterial* test antigens, Vaccine, 2007, 25:1553-1566.
Sherman, "Regulation of the *Mycobacterium tuberculosis* Hypoxic Response Gene Encoding -Crystallin", Proceedings of the National Academy of Sciences, 98(13):7534-7539 (Jun. 19, 2001).
Singhal, et al., Immunoprophylaxis of Tuberculosis: An update of Emerging Trends, Arch. Immunol. Ther. Exp., 2010, 58:97-106.
Sinigaglia, "A Malaria T-Cell Epitope Recognized in Association with Most Mouse and Human MHC Class II Molecules", Nature, 336(6201):778-780 (Dec. 22-29, 1988).
Skeiky, "Differential immune responses and protective efficacy induced by components of a tuberculosis polyprotein vaccine, Mtb72F, delivered as naked DNA or recombinant protein", The Journal of Immunology, 172(12):7618-7628 (Jun. 15, 2004).
Skeiky, et al., Advances in tuberculosis vaccine strategies, Nature Reviews/Microbiology, Jun. 2006, 4:469-476.
Skeiky, et al., Non-clinical efficacy and safety of HyVac4:IC31 vaccine administered in a BCG prime-boost regimen, Vaccine, 2010, 28:1084-1093.
Skjot, "Comparative Evaluation of Low-Molecular-Mass Proteins form *Mycobacterium tuberculosis* Identifies Members of the ESAT-6 Family as Immunodominant T-Cell Antigens", Infection and Immunity, 68(1):214-220 (Jan. 2000).
Stockinger, "CD4+ memory T cells: functional differentiation and homeostasis", Immunology Reviews, 211:39-48 (Jun. 2006).
Stryhn, "Peptide binding specificity of major histocompatibility complex class I resolved into an array of apparently independent subspecificities: quantitation by peptide libraries and improved prediction of binding", The European Journal of Immunology, 26(8):1911-1918 (Aug. 1996).
Theisen, "Antigenicity and Immunogenicity of Recombinant Glutamate-Rich Protein of *Plasmodium falciparum* Expressed in *Escherichia coli*", Clinical and Diagnostic Laboratory Immunology, 2(1):30-34 (Jan. 1995).

(56) References Cited

OTHER PUBLICATIONS

Thompson, "Clustal W: Improving the Sensitivity of Progressive Multiple Sequence Alignment Through Sequence Weighting, Position-Specific Gap Penalties and Weight Matrix Choice", Nucleic Acids research, 22(22):4673-4680 (Nov. 11, 1994).
Ulmer, "Polynucleotide Vaccines", Current Opinion in Investigational Drugs, 2(9):983-989 (1993).
US FDA "Guidance for industry: Estimating the Maximum Safe Starting Dose in initial clinical trials for therapeutics in adult healthy volunteers", U.S. Department of Health and Human Services, Food and Drug Administration, Center for Drug Evaluation and Research (Jul. 2005).
Van Pinxteren, "Control of Latent *Mycobacterium tuberculosis* Infection is Dependent on CD8 T Cells", The European Journal of Immunology, 30(12):3689-3698 (Dec. 2000).
Vordermeier, "Correlation of ESAAT-6—Specific Gamma Interferon Production with Pathology in Cattle Following *Mycobacterium bovis* BCG Vaccination against Experimental Bovine Tuberculosis", Infection and Immunity, 70(6):3026-3032 (Jun. 2002).
Wang, "Tuberculosis vaccines: the past, present and future", Expert Reviews Vaccines, 1(3):341-54 (Oct. 2002).
World Health Organization, "Global Tuberculosis Control", WHO Report, Geneva, Switzerland, WHO/CDS/TB/2001.287, 1-42 (2001).
Wu, et al., Distinct Lineages of $T_H$ I Cells Have Differential Capacities for Memory Cell Generation in Vivo, Nature Immunology, 3(9): 852-858 (Sep. 2002) Epublication: Aug. 12, 2002.
Office Action dated Jun. 21, 2005 issued in U.S. Appl. No. 10/617,038.
Response dated Aug. 11, 2005 to Office Action issued in U.S. Appl. No. 10/617,038.
Office Action dated Oct. 26, 2005 issued in U.S. Appl. No. 10/617,038.
Response dated Jan. 18, 2006 to Office Action issued in U.S. Appl. No. 10/617,038.
Office Action dated Apr. 12, 2006 issued in U.S. Appl. No. 10/617,038.
Response dated Jul. 17, 2006 to Office Action issued in U.S. Appl. No. 10/617,038.
Office Action dated Jan. 17, 2007 issued in U.S. Appl. No. 10/617,038.
Response dated May 15, 2007 to Office Action issued in U.S. Appl. No. 10/617,038.
Office Action dated Aug. 2, 2007 issued in U.S. Appl. No. 10/617,038.
Response dated Aug. 10, 2007 to Office Action issued in U.S. Appl. No. 10/617,038.
Office Action dated Oct. 30, 2007 issued in U.S. Appl. No. 10/617,038.
Response dated Jan. 11, 2008 to Office Action issued in U.S. Appl. No. 10/617,038.
Office Action dated May 19, 2008 issued in U.S. Appl. No. 10/617,038.
Response dated Aug. 27, 2008 to Office Action issued in U.S. Appl. No. 10/617,038.
Office Action dated Dec. 8, 2008 issued in U.S. Appl. No. 10/617,038.
Response dated Feb. 9, 2009 to Office Action issued in U.S. Appl. No. 10/617,038.
Office Action dated Mar. 9, 2009 issued in U.S. Appl. No. 10/617,038.
Response dated May 7, 2009 to Office Action issued in U.S. Appl. No. 10/617,038.
Office Action dated Aug. 5, 2009 issued in U.S. Appl. No. 10/617,038.
Response dated Dec. 8, 2009 to Office Action issued in U.S. Appl. No. 10/617,038.
Office Action dated Feb. 22, 2010 issued in U.S. Appl. No. 10/617,038.
Office Action dated Aug. 1, 2011 issued in U.S. Appl. No. 12/785,053.
Response dated Oct. 26, 2011 to Office Action issued in U.S Appl. No. 12/785,053.
Office Action dated Mar. 1, 2011 issued in U.S. Appl. No. 12/500,881.

* cited by examiner

Fig 1A
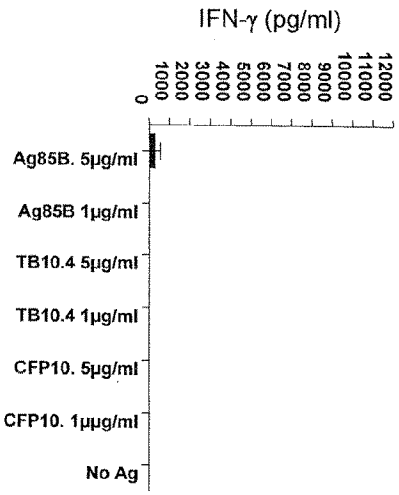
Fig1C
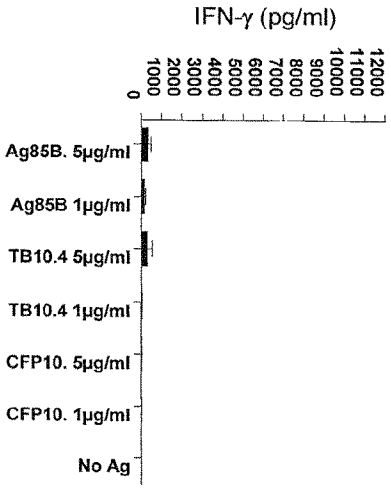
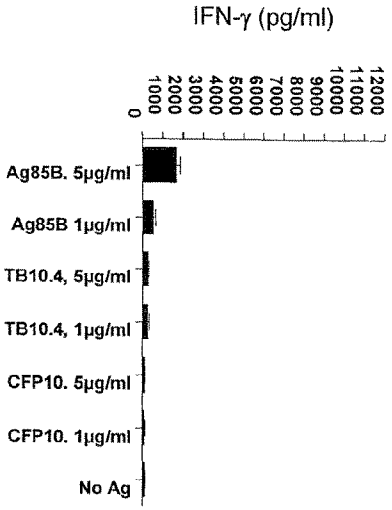
Fig 1B
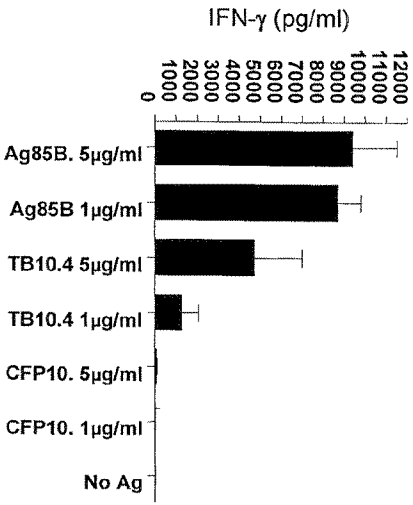
Fig 1D

VACCINES COMPRISING TB10.4

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a division of U.S. patent application Ser. No. 12/500,881, filed Jul. 10, 2009, which claims the benefit under 35 USC 119(e) of prior U.S. Provisional Patent Application No. 61/085,973, filed Aug. 4, 2008, which applications are incorporated herein by reference.

BACKGROUND OF THE INVENTION

The global effort to develop a more effective Mycobacterium tuberculosis (M. tuberculosis) vaccine than the currently used Bacillus of Calmette and Guerin (BCG) vaccine involves different strategies such as live attenuated vaccines (Horwitz, et al., 2000), virally vectored M. tuberculosis vaccines (McShane, et al., 2004), and subunit vaccines (Olsen, et al., 2001 and Skeiky, et al., 2004). The subunit approach holds a number of advantages, such as increased safety and stability as well as the demonstrated ability to boost prior BCG vaccination (Brandt, et al., 2004; Dietrich, et al., 2006). In addition, as subunit vaccines appear not to be influenced by environmental mycobacteria, this type of vaccine may be of particular use in the developing world (Brandt, et al., 2002). However, progress in this field has been delayed by the lack of adjuvants that induce a strong cell-mediated immune (CMI) response. Therefore, a need still remains for an immunogenic composition which can generate polyfunctional immune cells thereby providing greater protection against M. tuberculosis.

SUMMARY OF THE INVENTION

An immunogenic composition and vaccine for mammalian use with a low dose of an antigen comprising TB10.4 fused to a polypeptide of the antigen 85-complex (Ag85, composed of the Ag85A, Ag85B, and Ag85C proteins (Dietrich, et al., 2005)), e.g., Ag85B in an adjuvant, and methods of immunization and treatment of M. tuberculosis, are provided.

An immunogenic composition for mammalian use is provided comprising a TB10.4 protein and an Ag85-complex protein (described herein), which optionally can be fused together or provided as separate proteins, wherein the total amount of protein is less than about 25 μg, or less than 10 μg or equal to about 0.5 μg per antigen dose. In a further embodiment, the composition is for human use. In one embodiment, the composition does not contain dimethyl dioctadecyl ammonium bromide (DDA). An immunogenic composition described herein can additionally comprise an adjuvant. In one embodiment, the adjuvant has at least one polycationic peptide and at least one oligonucleotide, and in a further embodiment the oligonucleotide is a TLR9 (toll-like receptor 9) agonist. In one embodiment, the adjuvant is IC31® adjuvant (described herein). In a further embodiment, the protein is from the Ag85-complex is an Ag85B protein.

In another embodiment, a vaccine is provided for mammalian use which comprises the above mentioned immunogenic composition. In a further embodiment, the vaccine is for human use. In still another embodiment, a method of inducing protection against M. tuberculosis in a mammal is provided, the method comprising introducing into the mammal an immunogenic composition as described above. In a further embodiment, the method is for inducing protection in a human.

Still other aspects and embodiments of the invention will be apparent from the detailed description of the invention.

BRIEF DESCRIPTION OF THE DRAWINGS

FIGS. 1A-1D illustrate the concentration of IFN-γreleased upon stimulation of peripheral blood mononuclear cells (PBMCs) with either 1 or 5 μg/ml of Ag85B, TB10.4, control antigen CFP10, or no antigen. Stimulation is post-vaccination with varying doses of Ag85B-TB10.4 (Hyvac4, i.e., H4) formulated in IC31® adjuvant −15 μg H4 (FIG. 1C), 5 μg H4 (FIG. 1B), 0.5 μg H4 (FIG. 1D), or control (FIG. 1A). Values represent the means of triplicate and SEMs are indicated by bars.

FIGS. 3A and 3B reflect data obtained from two experiments (repeated). The groups of mice reflected are non-vaccinated (negative control), Bacillus of Calmette and Guerin (BCG) immunized (positive control), 0.5 μg H4 (Ag85B-TB10.4 fusion protein in IC31® adjuvant), 5 μg H4, and 15 μg H4. Following challenge with aerosolized virulent M. tuberculosis (Erdman strain), colony forming units (CFU) in the lungs were determined. $Log_{10}$ CFU is reflected for each group.

DETAILED DESCRIPTION OF THE INVENTION

Figure 2A:
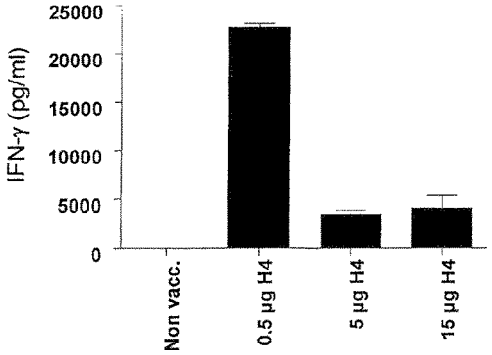
FIGS. 2A-2D illustrate IFN-γ released upon stimulation of PBMC's (FIG. 2A)/(FIG. 2C) and splenocytes (FIG. 2B)/(FIG. 2D) with Ag85B (FIG. 2A)/(FIG. 2B) or TB10.4 (FIG. 2C)/(FIG. 2D), post-vaccination with 0.5 μg, 5 μg, or 15 μg or 0 μg (non-vacc.) of H4 formulated in IC31® adjuvant. In (FIG. 2A)-(FIG. 2D), a vaccination dose of 0.5 μg H4 gave significantly ($p<0.05$, one-way ANOVA and Tukey's post test) higher antigen responses, compared to vaccination doses of 5 μs and 15 μg.
Figure 2C:
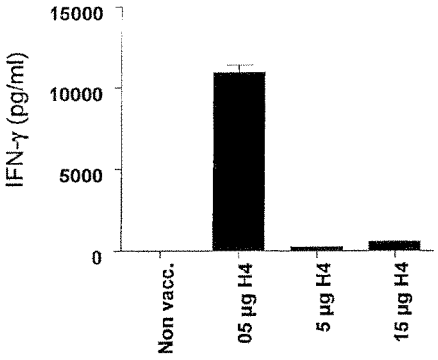
Figure 2B:
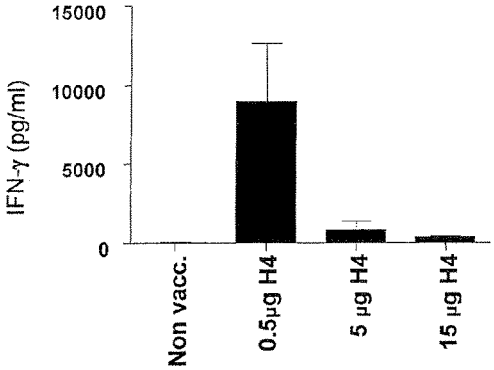
Figure 2D:
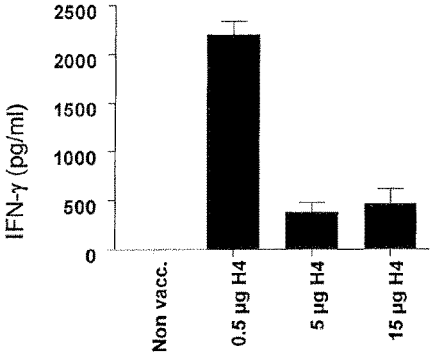

The combination of Ag85B-TB10.4 (Hyvac 4) and the IC31® adjuvant as an immunogenic composition and as a new vaccine against infection of mammals with M. tuberculosis is provided. In a further embodiment, an immunogenic composition or vaccine as described herein is effective against infection in humans. Ag85B-TB10.4 and the IC31® adjuvant induces high amounts of polyfunctional $CD4^+$ T cells and provides significant protection against M. tuberculosis. Surprisingly, the combination of the Ag85B-TB10.4 antigen and the IC31® adjuvant was sensitive to the antigen dose. Thus, whereas a standard dose in mice of 5 μg of Ag85B-TB10.4 in IC31® adjuvant did not lead to protection against M. tuberculosis, 0.5 μg Ag85B-TB10.4 in IC31® adjuvant induced protection comparable to that of Bacillus of Calmette and Guerin (BCG).

In an effort to generate an efficient vaccine against infection of mammals with M. tuberculosis, the combination of the Ag85B-TB10.4 fusion protein and IC31® adjuvant is used in one or more embodiments. Ag85B-TB10.4 fusion protein has the advantage that it does not include any of the proteins that are useful for diagnostic purposes such as, e.g., ESAT-6. The absence of ESAT-6 in a vaccine as described herein will allow diagnostic tests and a vaccine to be used in parallel since the Ag85B-TB10.4 fusion protein does not compromise any of the specific diagnostic tests. In one embodiment, a vaccine described herein contains an Ag85 protein and TB10.4 as the sole antigens. In a further embodiment, a vaccine described herein contains the fusion of Ag85B-TB10.4 as the sole antigen.

In another embodiment, the vaccine excludes (does not contain) dimethyl dioctadecyl ammonium bromide (DDA). In yet another embodiment, the vaccine excludes (does not contain) monophosphoryl lipid A (MPL). In another embodiment, the vaccine excludes (does not contain) DDA or MPL. In another embodiment, the vaccine contains a mixture a polycationic peptide and oligodeoxynucleic molecules. In a further embodiment, the vaccine contains a mixture of peptide $NH_2$-KLKLLLLLKLK-COOH (SEQ ID NO:1) and oligonucleotide 5'-ICI CIC ICI CIC ICI CIC ICI CIC IC-3' (SEQ ID NO:2)$(dIdC)_{13}$ (ODN1a; polydeoxyinosinic-deoxycytidylic acid; oligo$(dIdC)_{13}$) as the sole adjuvant. In a further embodiment, the vaccine contains IC31® adjuvant as the sole adjuvant.

The Ag85B-TB10.4 fusion protein in the IC31® adjuvant constitutes an effective vaccine against infection in mammals with M. tuberculosis. In a further embodiment, the vaccine is effective against infection in humans.

In one embodiment, a vaccine as described is useful as a BCG booster vaccine.

In another embodiment, the Ag85B-TB10.4 fusion protein in the IC31® adjuvant constitutes an effective vaccine against infection with M. tuberculosis. The Ag85B-TB10.4 and IC318 combination induces a high amount of polyfunctional $CD4^+$ T cells and provides significant protection against M. tuberculosis. Surprisingly, the combination of the Ag85B-TB10.4 fusion protein and the IC31® adjuvant is extremely sensitive to the antigen dose. Whereas a dose of 5 μg of Ag85B-TB10.4 in IC31® adjuvant does not lead to significant protection against M. tuberculosis, 0.5 μg Ag85B-TB10.4 in IC31® adjuvant induces a strong protection comparable to that of BCG (Ex. 3). Applicants have identified that Ag85B-TB10.4 is an extraordinarily immunogenic molecule.

In one embodiment, the application is directed to the combination of an Ag85B-TB10.4 (Hyvac 4; H4) fusion protein and IC31® adjuvant as a new vaccine against infection with M. tuberculosis. The IC31® adjuvant comprises cationic peptides and is a TLR9 (toll-like receptor 9) agonist.

A vaccine for mammalian use with a low dose of an antigen comprising TB10.4 fused to a polypeptide of the antigen 85-complex, e.g., Ag85B in an adjuvant, and methods of immunization against, and treatment of, M. tuberculosis, are provided. In a further embodiment, the vaccine is for human use.

An immunogenic composition for mammalian use is provided comprising a TB10.4 protein and an Ag85-complex protein which optionally can be fused together or provided as separate proteins wherein the total amount of protein is less than about 25 μg, or less than 10 μg or equal to about 0.5 μg per antigen dose. In a further embodiment, the immunogenic composition is for human use. In still another embodiment, the composition excludes (does not contain) ESAT-6. In one embodiment, a composition described herein contains an Ag85 protein and TB10.4 as the sole antigens. In a further embodiment, a composition described herein contains the fusion of Ag85B-TB10.4 as the sole antigen.

In a further embodiment, the composition excludes (does not contain) dimethyl dioctadecyl ammonium bromide (DDA). In another embodiment, the composition excludes (does not contain) monophosphoryl lipid A (MPL). In another embodiment, the composition excludes (does not contain) DDA or MPL. In another embodiment, the composition contains a mixture a polycationic peptide and oligodeoxynucleic molecules. In a further embodiment, the composition contains a mixture of peptide $NH_2$-KLKLLLLLKLK-COOH (SEQ ID NO:1) and oligonucleotide 5'-ICI CIC ICI CIC ICI CIC ICI CIC IC-3' (SEQ ID NO:2)$(dIdC)_{13}$ (ODN1a; polydeoxyinosinic-deoxycytidylic acid; oligo$(dIdC)_{13}$) as the sole adjuvant. In a further embodiment, the composition contains IC31® adjuvant as the sole adjuvant.

An immunogenic composition described herein can additionally comprise an adjuvant. In one embodiment, the adjuvant has at least one polycationic peptide and at least one oligonucleotide, and in a further embodiment the oligonucleotide is a TLR9 agonist.

In one embodiment, the adjuvant is IC31®. In a further embodiment, the protein from the Ag85-complex is an Ag85B protein.

Also described is a vaccine for mammalian use comprising an immunogenic composition described herein. In a further embodiment, the vaccine is for human use.

In another embodiment, a method of inducing protection against M. tuberculosis in a mammal is provided, the method comprising introducing into the mammal an immunogenic composition as described herein. In another embodiment, a method of inducing polyfunctional $CD4^+$ T cells in a mammal is provided, the method comprising introducing into the mammal an immunogenic composition as described herein. In another embodiment, a method of inducing an immune response against M. tuberculosis in a mammal is provided, the method comprising introducing into the mammal an immunogenic composition as described above. In further embodiments of these methods, the mammal is a human.

Throughout this specification, unless the context requires otherwise, the word "comprise", or variations thereof such as "comprises" or "comprising", will be understood to mean the inclusion of a stated element or integer or group of elements or integers but not the exclusion of any other element or integer or group of elements or integers. Unless otherwise indicated, the term "about" means±10% the limit of weight measurement given.

A. Antigens

In one embodiment, the antigen may comprise a protein of the Ag85-complex fused to TB10.4 protein (TB10.4 described in Dietrich, et al., 2005), including, for example, proteins Ag85A, Ag85B or Ag85C of the Ag85 complex. The proteins of the antigen 85 complex (85A, 85B, and 85C) are encoded by three genes located at different sites in the mycobacterial genome, which show extensive cross-reactivity as well as homology at amino acid and gene levels. The proteins differ slightly in molecular mass in the 30- to 31-kDa region. The individual components of the Ag85 complex (Ag85A, Ag85B and Ag85C) are publicly available (e.g., from Colorado State University).

In one embodiment, a fusion protein of the TB10.4 protein and an Ag85-complex protein may be prepared as described in [Dietrich, et al., 2005]. In another embodiment, a fusion may be prepared by linking the TB10.4 protein to an Ag85-complex protein directly or via a connecting linker of at least one amino acid. Other methods of preparing the fusion proteins are known conventionally, and are considered to be useful herein.

In another embodiment, Ag85B-TB10.4 is utilized. In a further embodiment, Ag85B-TB10.4 is given in low doses, i.e., doses less than those currently used in subunit M. tuberculosis vaccines (e.g., 5 μg to 25 μg per dose), to initiate the maximum amount of polyfunctional immune cells, inducing more interferon-γ expression and increased protection against M. tuberculosis. Throughout this specification Ag85B-TB10.4 fusion protein is interchangeable with the terms H4 and HyVac4.

In another embodiment the antigen may comprise a protein of the Ag85 complex and TB10.4 protein wherein the Ag85 complex protein is not fused to the TB10.4 protein. In a further embodiment, the protein of the Ag85 complex is Ag85B. In one embodiment, the Ag85B-TB10.4 fusion protein is prepared according to Dietrich, et al., 2005.

In still another embodiment, the antigen excludes (does not contain) ESAT-6.

| Protein | amino acid sequence |
|---|---|
| Ag85A (SEQ ID NO: 3) | MQLVDRVRGA VTGMSRRLVV GAVGAALVSG LVGAVGGTAT AGAFSRPGLP VEYLQVPSPS MGRDIKVQFQ SGGANSPALY LLDGLRAQDD FSGWDINTPA FEWYDQSGLS VVMPVGGQSS FYSDWYQPAC GKAGCQTYKW ETFLTSELPG WLQANRHVKP TGSAVVGLSM AASSALTLAI YHPQQFVYAG AMSGLLDPSQ AMGPTLIGLA MGDAGGYKAS DMWGPKEDPA WQRNDPLLNV GKLIANNTRV WVYCGNGKPS DLGGNNLPAK FLEGFVRTSN IKFQDAYNAG GGHNGVFDFP DSGTHSWEYW GAQLNAMKPD LQRALGATPN TGPAPQGA |
| Ag85B (SEQ ID NO: 4) | MTDVSRKIRA WGRRLMIGTA AAVVLPGLVG LAGGAATAGA FSRPGLPVEY LQVPSPSMGR DIKVQFQSGG NNSPAVYLLD GLRAQDDYNG WDINTPAFEW YYQSGLSIVM PVGGQSSFYS DWYSPACGKA GCQTYKWETF LTSELPQWLS ANRAVKPTGS AAIGLSMAGS SAMILAAYHP QQFIYAGSLS ALLDPSQGMG PSLIGLAMGD AGGYKAADMW GPSSDPAWER NDPTQQIPKL VANNTRLWVY CGNGTPNELG GANIPAEFLE NFVRSSNLKF QDAYNAAGGH NAVFNFPPNG THSWEYWGAQ LNAMKGDLQS SLGAG |
| Ag85C (SEQ ID NO: 5) | MTFFEQVARL RSAATTLPRR LAIAAMGAVL VYGLVGTFGG PATAGAFSRP GLPVEYLQVP SASMGRDIKV QFQGGGPHAV YLLDGLRAQD DYNGWDINTP AFEEYYQSGL SVIMPVGGQS SFYTDWYQPS QSNGQNYTYK WETFLTREMP AWLQANKGVS PTGNAAVGLS MSGGSALILA AYYPQQFPYA ASLSGFLNPS EGWWPTLIGL AMNDSGGYNA NSMWGPSSDP AWKRNDPMVQ IPRLVANNTR IWVYCGNGTP SDLGGDNIPA KFLEGLTLRT NQTFRDTYAA DGGRNGVFNF PPNGTHSWPY WNEQLVAMKA DIQHVLNGAT PPAAPAAPAA |
| TB10.4 (SEQ ID NO: 6) | MSQIMYNYPA MLGHAGDMAG YAGTLQSLGA EIAVEQAALQ SAWQGDTGIT YQAWQAQWNQ AMEDLVRAYH AMSSTHEANT MAMMARDTAE AAKWGG |

Each protein may be modified by glycosylation, or lipidation (Mowat, et al., 1991; Lustig, et al., 1976). Each protein may be modified by the addition of prosthetic groups, a purification moiety, or a signal peptide. Each protein may be modified one or more times or not undergo any modification. Each protein may be modified singly or in combination. Each protein will be characterised by specific amino acids and be encoded by specific nucleic acid sequences. Within the scope of the present invention are such sequence and analogues and variants produced by recombinant or synthetic methods wherein such amino acid sequences have been modified by substitution, insertion, addition or deletion of one or more amino acid residues in the recombinant protein while retaining immunogenicity as confirmed by any one or all of the biological assays described herein.

Substitutions are preferably "conservative". These are defined according to the following table. Amino acids in the same block in the second column and preferably in the same line in the third column may be substituted for each other. The amino acids in the third column are indicated in one-letter code.

| | | |
|---|---|---|
| ALIPHATIC | Non-polar | G, A, P<br>I, L, V |
| | Polar-uncharged | C, S, T, M<br>N, Q |
| | Polar-charged | D, E<br>K, R |
| AROMATIC | | H, F, W,Y |

B. Adjuvants

In one embodiment, the antigen comprises an Ag85 complex protein fused to TB10.4 protein in an adjuvant. In another embodiment, the antigen comprises an Ag85 complex protein and a TB10.4 protein (i.e., non-fused) in an adjuvant.

Ag85B-TB10.4 is an extraordinary immunogenic molecule which must be given in low doses to initiate the maximum amount of polyfunctional immune cells inducing more interferon-γ expression and increased protection against M. tuberculosis. It is exemplified with an adjuvant comprising a polycationic peptide [e.g., polylysine (KLK peptide) or polyarginine] and oligodeoxynucleic molecules but is not limited to this adjuvant.

In a further embodiment, the adjuvant is a mixture of a polycationic peptide [e.g., polylysine (KLK peptide) or polyarginine] and oligodeoxynucleic molecules [I-ODNs]. An example of a suitable I-ODN for use with the current invention is oligo dIC, e.g., oligonucleotide 5'-ICI CIC ICI CIC ICI CIC ICI CIC IC-3' (SEQ ID NO:2)$(dIdC)_{13}$ (ODN1a; polydeoxyinosinic-deoxycytidylic acid; oligo $(dIdC)_{13}$). I-ODN's appropriate for use in the embodiments described herein may be found in International (PCT) Patent Application Publication Nos.: WO 01/93905 and WO 01/93903, which are hereby incorporated by reference. An example of KLK peptides suitable for use with the current invention are $NH_2$-KLKLLLLLKLK-COOH (SEQ ID NO:1) or KLKLLLLLKLK-$NH_2$ (SEQ ID NO:1). Additional examples of appropriate polycationic peptides are RLRLLLLLRLR-$NH_2$ (SEQ ID NO:7), RLKLLLLLKLR-$NH_2$ (SEQ ID NO:8), KFKFFFFFKFK-$NH_2$ (SEQ ID NO:9), KWKWWWWWKWK-$NH_2$ (SEQ ID NO:10) or KVKVVVVVKVK-$NH_2$ (SEQ ID NO:11). Polycationic peptides suitable for use in these embodiments may be found in International (PCT) Patent Application Publication No. WO/0232451, which is hereby incorporated by reference.

As described herein, the IC31® adjuvant (Intercell AG) comprises a mixture of the peptide $NH_2$-KLKLLLLLKLK-COOH (SEQ ID NO:1) (Multiple Peptide Systems, San Diego, Calif., USA) and the oligonucleotide 5'-ICI CIC ICI CIC ICI CIC ICI CIC IC-3' (SEQ ID NO:2)$(dIdC)_{13}$ (ODN1a; polydeoxyinosinic-deoxycytidylic acid; oligo $(dIdC)_{13}$) (Proligo, Boulder, USA).

In one embodiment, a dose of 0.5 μg Ag85B-TB10.4 fusion protein in IC31® adjuvant [100 nmol peptide ($NH_2$-

KLKLULLKLK-COOH (SEQ ID NO:1) and 5 nmol oligonucleotide 5'-ICI CIC ICI CIC ICI CIC ICI CIC IC-3' (SEQ ID NO:2)$(dIdC)_{13}$] induces a strong INF-γ response. However, one of skill in the art will be able to adjust amounts and concentrations according to the application. This strong IFN-γ response is in approximately the same range as 5 μg Ag85B-TB10.4 fusion protein, without IC31® adjuvant. In a further embodiment, 0.5 μg Ag85B-TB10.4 fusion protein in IC31® adjuvant [100 nmol peptide ($NH_2$-KLKLLLLLKLK-COOH (SEQ ID NO:1) and 5 nmol oligonucleotide 5'-ICI CIC ICI CIC ICI CIC ICI CIC IC-3' (SEQ ID NO:2)$(dIdC)_{13}$] is utilized. This provides a strong protection in approximately the same range as BCG. Without wishing to be bound by theory, Applicants have determined that this is surprisingly better than 5 μg or 15 μg of Ag85B-TB10.4 fusion protein alone (i.e., no IC31® adjuvant), revealing that the preferred dose of Ag85B-TB10.4 fusion protein alone may be lower.

In one embodiment, less than 5 μg of Ag85B-TB10.4 fusion protein per dose is utilized. In still other embodiments, 1 μg, 0.5 μg, or 0.1 μg of Ag85B-TB10.4 fusion protein is utilized.

As reflected herein, the lowest dose of Ag85B-TB10.4 fusion protein (0.5 μg) in IC31® adjuvant gave the highest IFN-γ response after stimulation with either of the vaccine components (see FIGS. 1A-1D and 2A-2D). Finally, vaccination with Ag85B-TB10.4 fusion protein in IC31® adjuvant induced two major $CD4^+$ T cell populations, one expressing IFN-γ, IL-2, and TNF-α, and another expressing IL-2 and TNF-α. Both of these T cell populations belong to central memory T cells, and are necessary for long term memory. Importantly, as seen with the IFN-γ expression measured by ELISA, using a dose of 0.5 μg HyVac4 fusion protein in IC31® adjuvant induced the highest cell numbers within the polyfunctional population that expressed IFN-γ, IL-2, and TNF-α.

Applicants have determined that the adjuvants IC31® and cationic liposomes exhibit different sensitivities towards the antigen dose; and that the preferred antigen dose in IC31® adjuvant is antigen-dependent.

Figure 3A:
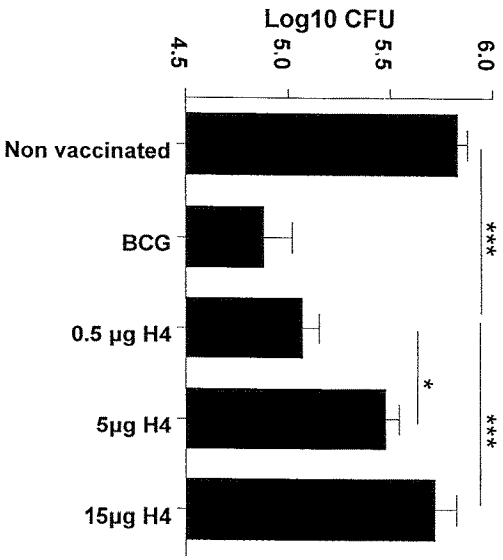
FIGS. 3A and 3B illustrate the protective efficacy of H4.
Figure 3B:
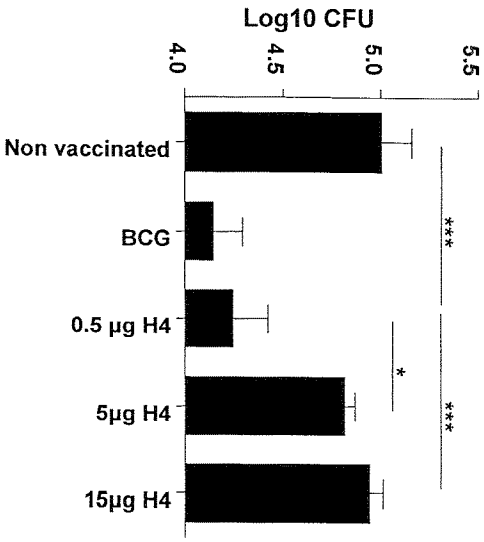

0.5 μg Ag85B-TB10.4 fusion protein in IC31® adjuvant induced significant protection whereas 5 μg Ag85B-TB10.4 fusion protein in IC31® adjuvant did not (FIGS. 3A-3B). One of skill in the art will recognize from this application that the appropriate antigen dose in a vaccine depends both on the antigen and on the adjuvant.

In one embodiment, the composition excludes (does not contain) dimethyl dioctadecyl ammonium bromide (DDA). In another embodiment, the composition excludes (does not contain) monophosphoryl lipid A (MPL).

The following examples are illustrative of the compositions and methods of the invention. It will be readily understood by one of skill in the art that the specific conditions described herein can be varied without departing from the scope of the present invention. It will be further understood that other compositions not specifically illustrated are within the scope of the invention as defined herein.

EXAMPLES

The following information is supportive of the examples that follow.

Animals:

Studies were performed with 8 to 12 week-old C57BL/6xBalb/c F1 female mice, purchased from Taconic, Ejby, Denmark. Infected animals were housed in cages contained within laminar flow safety enclosures in a BSL-3 facility. The use of mice was in accordance with the regulations set forward by the Danish Ministry of Justice and Animal Protection Committees and in compliance with EC Directive 86/609 and the US ALAC recommendations for the care and use of Laboratory animals.

Bacteria:

M. tuberculosis Erdman were grown at 37° C. on Löwenstein-Jensen medium or in suspension in Sauton medium enriched with 0.5% sodium pyruvate and 0.5% glucose.

Immunization:

Mice were immunized three times at 2-week intervals subcutaneously on the back with experimental vaccines containing 0.5, 5 or 15 μg of Ag85B-TB10.4 fusion protein (H4)/dose, emulsified in IC31® adjuvant in a total volume of 0.2 ml/dose. Doses were 100 nmol peptide and 5 nmol oligonucleotide. All vaccines were formulated using 10 mM Tris-HCl/270 mM sorbitol buffer (pH 7.9) as previously described (Olsen, et al., 2001) to obtain a final volume of 0.2 ml/mouse. At the time of the first subunit vaccination, one group of mice received a single dose of BCG Danish 1331 ($2.5\times10^5$ CFU) injected subcutaneously at the base of the tail and one group received a saline injection. All groups of mice were challenged 10 weeks after the first vaccination.

Experimental Infections:

When challenged by the aerosol route, the animals were infected with approximately 50 CFU of M. tuberculosis Erdman/mouse. These mice were sacrificed 6 weeks after challenge. Numbers of bacteria in the spleen or lung were determined by serial threefold dilutions of individual whole-organ homogenates in duplicate on 7H11 medium (Middlebrook; Sigma-Aldrich). Organs from the BCG-vaccinated animals were grown on medium supplemented with 2 μg of 2-thiophene-carboxylic acid hydrazide (TCH)/ml to selectively inhibit the growth of the residual BCG bacteria in the test organs. Colonies were counted after 2 to 3 weeks of incubation at 37° C. Bacterial burden in the lungs was expressed as $\log_{10}$ of the bacterial counts based on vaccination groups of six animals.

Lymphocyte Cultures:

Lymphocytes from spleens were obtained as described previously (Brandt, et al.). Blood lymphocytes (PBMCs) were purified on a density gradient. Cells pooled from five mice in each experiment were cultured in microtiter wells (96-well plates; Nunc, Roskilde, Denmark) containing $2\times10^5$ cells in a volume of 2000 of RPMI 1640 supplemented with $5\times10^{-5}$ M 2-mercaptoethanol, 1% penicillin-streptomycin, 1 mM glutamine, and 5% (vol/vol) fetal calf serum. Based on previous dose-response investigations, the mycobacterial antigens were all used at 15 μg/ml or 5 μg/ml, while concanavalin A was used at a concentration of 1 μg/ml as a positive control for cell viability. All preparations were tested in cell cultures and found to be nontoxic at the concentrations used in the present study. Supernatants were harvested from cultures after 72 h of incubation for the investigation of IFN-γ.

IFN-γ Enzyme-Linked Immunosorbent Assay (ELISA):

Microtiter plates (96 wells; Maxisorb; Nunc) were coated with monoclonal hamster anti-murine IFN-γ (Genzyme, Cambridge, Mass.) in PBS at 4° C. Free binding sites were blocked with 1% (wt/vol) bovine serum albumin-0.05% Tween 20. Culture supernatants were tested in triplicate, and IFN-γ was detected with a biotin-labelled rat anti-murine monoclonal antibody (clone XMG1.2; Pharmingen, San Diego, Calif.). Recombinant IFN-γ (Pharmingen, San Diego, Calif.) was used as a standard.

FACS Analysis of Lymphocytes:

Intracellular cytokine staining procedure: Cells from blood, spleen or lungs of mice were stimulated for 1-2 h with 2 μg/ml Ag and subsequently incubated for 6 h with 10 μg/ml brefeldin A (Sigma-Aldrich, USA) at 37° C. Thereafter, cells were stored overnight at 4° C. The following day, Fc receptors were blocked with 0.54 ml anti-CD16/CD32 mAb (BD Pharmingen, USA) for 10 minutes, where after the cells were washed in FACS buffer (PBS containing 0.1% sodium azide and 1% FCS), and stained for surface markers as indicated using 0.2 μg/ml anti-CD4 (clone: RM4-5), anti-CD8 (clone: 53-6,7) mAb's. Cells were then washed in FACS buffer, permeabilized using the Cytofix/Cytoperm™ kit (BD Pharmingen, Denmark) according to the manufacturers instructions, and stained intracellularly with 0.2 μg/ml anti-IFN-γ (clone: XMG1.2), anti-TNF-α (clone: MP6-XT22), or anti-IL-2 (clone: JES6-5H4) mAb's. After washing, cells were re-suspended in formaldehyde solution 4% (w/v) pH 7.0 (Bie & Berntsen, Denmark) and analysed by flow cytometry on a six-colour BD FACSCanto flow cytometer (BD Biosciences, USA).

Statistical Methods:

The data obtained were tested by analysis of variance. Differences between means were assessed for statistical significance by Tukey's test. A P value of <0.05 was considered significant.

Example 1

Immune Response Induced after Immunization with Ag85B-TB10.4 Fusion Protein in IC31® Adjuvant The immunogenicity of Ag85B-TB10.4 fusion protein delivered in IC31® adjuvant was analyzed, including whether both components of the fusion protein were recognized by the immune system after immunization.

PBMC's isolated from groups of mice vaccinated with different doses of H4 in IC31® adjuvant and a saline control group were stimulated with either 1 or 5 μg/ml of Ag85B, TB10.4 or CFP10 (a Mycobacterium tuberculosis-specific antigen). After 72 hours the concentration of cell released IFN-γ was determined by ELISA. PBMC's were isolated 1 week after third vaccination and were pooled from five mice per group. Values in FIGS. 1A-1D represent the means of triplicate and SEM's are indicated by bars.

Groups of mice were immunized with Ag85B-TB10.4 fusion protein in IC31® adjuvant. As negative control, a group of mice received the adjuvant alone (data not shown). To examine antigen dose in IC31® adjuvant, we used 15, 5 and 0.5 μg of Ag85B-TB10.4 fusion protein. One week after the last injection, mice were bled, and the IFN-γ release was evaluated after in vitro stimulation of purified PBMCs with different concentrations of Ag85B and TB10.4 proteins (5 μg/ml and 1 μg/ml) (FIG. 1A). Immunization with Ag85B-TB10.4 fusion protein in IC31® adjuvant induced a strong IFN-γ response specific for Ag85B and TB10.4 proteins (FIGS. 1B-1D). Surprisingly, this response was sensitive to the antigen immunization dose. Thus, the lowest dose of Ag85B-TB10.4 fusion protein in IC31® adjuvant gave the highest IFN-γ response after stimulation with either Ag85B (9401+/−3668 pg/ml IFN-γ) or TB10.4 (4694+/−3992 pg/ml IFN-γ) (FIG. 1D). Using a dose of 5 μg or 15 μg Ag85B-TB10.4 fusion protein significantly reduced the IFN-γresponse against both Ag85B and TB10.4 proteins relative to mice vaccinated with 0.5 μg Ag85B-TB10.4 fusion protein ($p<0.001$). This was particularly apparent for the high immunization dose −15 μg Ag85B-TB10.4 fusion protein per immunization dose (FIG. 1C)—which gave IFN-γ responses that did not differ from the observed responses in non-vaccinated mice (or in Ag85B-TB10.4 fusion protein vaccinated mice stimulated in vitro with control antigen CFP10).

The same dose dependency was subsequently repeated in an independent experiment where the immune responses were analyzed in both blood and spleen (FIGS. 2A-2D). PBMC's (2A)/(2C) and splenocytes (2B)/(2D) isolated from groups of mice immunized with 3 different doses of H4 formulated in IC31® adjuvant or a saline control group were stimulated with Ag85B (2A)/(2B) or TB10.4 (2C)/(2D) for 72 hours where after IFN-γ cytokine secretion was measured by ELISA. The bars represent means of 3 individual mice. SEMs are indicated. In FIGS. 2A-2D, a vaccination dose of 0.5 μg H4 gave significantly ($p<0.05$, one-way ANOVA and Tukey's post test) higher antigen responses, compared to vaccination doses of 5 μg and 15 μg.

These results show that the lowest dose of 0.5 μg Ag85B-TB10.4 fusion protein in IC31® adjuvant induced the strongest systemic response of the antigen doses tested.

Example 2

Vaccination with Ag85B-TB10.4 Fusion Protein in IC31® Adjuvant Induces Polyfunctional $CD4^+$T Cells The phenotype of the T cells induced by immunizing with Ag85B-TB10.4 fusion protein in IC31® adjuvant was analyzed. In particular, the ability of this vaccine to induce polyfunctional ($IFN\text{-}\gamma^+IL\text{-}2^+TNF\text{-}\alpha^+$) $CD4^+$ T cells was determined as these have been shown to correlate with protective immunity against infections such as Leishmania major and to faun the basis for a long lived memory response.

Ag85B and TB10.4 specific T cells are poly-functional. Production of IFN-γ, TNF-α and IL-2 was assessed following antigenic stimulation of PBMC's and spleenocytes 2 weeks post-vaccination by flow cytometry.

PBMC's from Ag85B-TB10.4 fusion protein in IC31® adjuvant vaccinated mice were stimulated in vitro with Ag85B or TB10.4 fusion protein and analyzed by flow cytometry for expression of CD4, CD8, TNF-γ, TNF-α, and IL-2. The results show that immunizing with Ag85B-TB10.4 fusion protein in IC31® adjuvant induced two major polyfunctional T cell populations; $CD4^+IFN\text{-}\gamma^+IL\text{-}2^+TNF\text{-}\alpha^+$ and $CD4^+IL\text{-}2^+TNF\text{-}\alpha^+$ T cells. This was seen for Ag85B and TB10.4 specific T cells. Interestingly, as observed in FIG. 1, there is a higher response in the group immunized with 0.5 μg HyVac4 in IC31® adjuvant compared to the group immunized with 5 μg HyVac4 fusion protein in IC31® adjuvant, and that the major difference was that the group being vaccinated with only 0.5 μg showed significantly more polyfunctional T cells. Taken together, immunizing with Ag85B-TB10.4 fusion protein in IC31® adjuvant induced polyfunctional $CD4^+$ T cells and confirmed that lowering the amount of Ag85B-TB10.4 fusion protein increased the immunogenicity of the vaccine in terms of not only IFN-γexpression but also the number of polyfunctional T cells.

Example 3

Protective Efficacy of Ag85B-TB10.4 Fusion Protein and IC31® Adjuvant in a Mouse M. Tuberculosis Infection Model The protective efficacy of Ag85B-TB10.4 fusion protein in IC31® adjuvant was examined, including whether the dose dependency regarding the immunogenicity of the vaccine was also reflected in the protective efficacy of the vaccine.

In two independent experiments (A and B) groups of mice were vaccinated with three different doses of H4 formulated in IC31® adjuvant and compared to saline and BCG-vaccinated controls.

Mice were vaccinated three times at two weeks interval with Ag85B-TB10.4 fusion protein in IC31® adjuvant. As a positive control for protection, a group of mice were immunized once with BCG.

Ten weeks after the first vaccination, the mice were challenged by the aerosol route with virulent M. tuberculosis Erdman. Six weeks post challenge, the mice were sacrificed and the numbers [bacterial burden (CFU)] were determined in the lungs. As observed with the immunogenicity of the vaccines, the lowest Ag85B-TB10.4 fusion protein immunization dose induced the highest protection. Thus, mice vaccinated with 0.5 μg Ag85B-TB10.4 fusion protein in IC31® adjuvant contained a bacterial number of 5.0+/−0.2 $Log_{10}$ CFU in the lungs. This was equal to the numbers observed in BCG vaccinated mice (4.90+/−0.35 $Log_{10}$ CFU), but significantly lower ($p<0.001$) compared to the bacterial numbers in non-vaccinated mice (5.83+/−0.12 $Log_{10}$ CFU) (FIG. 3A). In contrast, the bacterial numbers in mice vaccinated with 5 μg or 15 μg of Ag85B-TB10.4 fusion protein in IC31® adjuvant, were not significantly different from the levels found in the lungs of non-vaccinated mice (FIG. 3A). Repeating the experiment led to the same conclusion although the overall bacterial numbers were slightly lower in all the groups (FIG. 3B). Thus the ability of the vaccine, Ag85B-TB10.4 fusion protein in IC31® adjuvant, to induce protection against M. tuberculosis correlated with the immunogenicity of the vaccine, in terms of IFN-γproduction and the number of polyfunctional T cells, and was highest when the lowest antigen dose was used.

In both experiments, data are presented as mean values from six animals per group and standard errors of the means are indicated by bars. Statistical comparisons among the vaccination groups were done by one-way ANOVA and Tukey's post test. Significant differences are only shown for selected groups. ***: $p<0.001$, *: $p<0.05$.

The surprising in vivo results from these well recognized M. tuberculosis animal models, supports the use of the immunogenic compositions of the current invention as a M. tuberculosis vaccine in humans.

Example 4

Protective Efficacy of Ag85B-TB10.4 Fusion Protein and IC31® Adjuvant in a Clinical Trial In human clinical trials subjects will be vaccinated with less than about 5 μg to 25 μg of Ag85B-TB10.4 in IC31® adjuvant. This low dose of Ag85B-TB10.4 is in stark contrast with other subunit M. tuberculosis vaccines currently in clinical trials. For example, 40 μg of MTB72F in AS02A per dose (Leroux-Roels, et al., 2005) and 50 μg of Ag85B-ESAT-6 in IC31® adjuvant per dose (clinical data not published yet).

PUBLICATIONS

1. Agger, E. M., I. Rosenkrands, A. W. Olsen, G. Hatch, A. Williams, C. Kritsch, K. Lingnau, A. von Gabain, C. S. Andersen, K. S. Korsholm, and P. Andersen. 2006. Protective immunity to tuberculosis with Ag85B-ESAT-6 in a synthetic cationic adjuvant system IC31. Vaccine 24:5452-5460.
2. Brandt, L., M. Elhay, I. Rosenkrands, E. B. Lindblad, and P. Andersen. 2000. ESAT-6 subunit vaccination against Mycobacterium tuberculosis. Infect Immun 68:791-795.
3. Brandt, L., J. Feino Cunha, A. Weinreich Olsen, B. Chilima, P. Hirsch, R. Appelberg, and P. Andersen. 2002. Failure of the Mycobacterium bovis BCG vaccine: some species of environmental mycobacteria block multiplication of BCG and induction of protective immunity to tuberculosis. Infect Immun 70:672-678.
4. Brandt, L., Y. A. Skeiky, M. R. Alderson, Y. Lobet, W. Dalemans, O. C. Turner, R. J. Basaraba, A. A. Izzo, T. M. Lasco, P. L. Chapman, S. G. Reed, and I. M. Orme. 2004. The protective effect of the Mycobacterium bovis BCG vaccine is increased by coadministration with the Mycobacterium tuberculosis 72-kilodalton fusion polyprotein Mtb72F in M. tuberculosis-infected guinea pigs. Infect Immun 72:6622-6632.
5. Brock, I., K. Weldingh, E. M. Leyten, S. M. Arend, P. Ravn, and P. Andersen. 2004. Specific T-cell epitopes for immunoassay-based diagnosis of Mycobacterium tuberculosis infection. J Clin Microbiol 42:2379-2387.
6. Darrah, P. A., D. T. Patel, P. M. De Luca, R. W. Lindsay, D. F. Davey, B. J. Flynn, S. T. Hoff, P. Andersen, S. G. Reed, S. L. Morris, M. Roederer, and R. A. Seder. 2007. Multi-functional TH1 cells define a correlate of vaccine-mediated protection against Leishmania major. Nat Med 13:843-850.
7. Dietrich, J., C. Andersen, R. Rappuoli, T. M. Doherty, C. G. Jensen, and P. Andersen. 2006. Mucosal administration of Ag85B-ESAT-6 protects against infection with Mycobacterium tuberculosis and boosts prior bacillus Calmette-Guerin immunity. J Immunol 177:6353-6360.
8. Dietrich, J., C. Aagaard, R. Leah, A. W. Olsen, A. Stryhn, T. M. Doherty, and P. Andersen. 2005. Exchanging ESAT6 with TB10.4 in an Ag85B fusion molecule-based tuberculosis subunit vaccine: efficient protection and ESAT6-based sensitive monitoring of vaccine efficacy. J Immunol 174:6332-6339.
9. Horwitz, M. A., G. Harth, B. J. Dillon, and S. Maslesa-Galic. 2000. Recombinant bacillus calmette-guerin (BCG) vaccines expressing the Mycobacterium tuberculosis 30-kDa major secretory protein induce greater protective immunity against tuberculosis than conventional BCG vaccines in a highly susceptible animal model. Proc Natl Acad Sci U S A 97:13853-13858.
10. Lalvani, A., A. A. Pathan, H. McShane, R. J. Wilkinson, M. Latif, C. P. Conlon, G. Pasvol, and A. V. Hill. 2001. Rapid detection of Mycobacterium tuberculosis infection by enumeration of antigen-specific T cells. Am J Respir Crit Care Med 163:824-828.
11. Lustig T V, Rieger H L, Kraft S C, Hunter R, Rothberg R M. 1976, Cell Immunol 24(1):164-7.
12. McShane, H., A. A. Pathan, C. R. Sander, S. M. Keating, S. C. Gilbert, K. Huygen, H. A. Fletcher, and A. V. Hill. 2004. Recombinant modified vaccinia virus Ankara expressing antigen 85A boosts BCG-primed and naturally acquired antimycobacterial immunity in humans. Nat Med 10:1240-1244.
13 Mowat A M, Donachie A M, Reid G, Jarrett 0.1991, Immunology 72(3):317-22
14. Olsen, A. W., L. A. van Pinxteren, L. M. Okkels, P. B. Rasmussen, and P. Andersen. 2001. Protection of mice with a tuberculosis subunit vaccine based on a fusion protein of antigen 85b and esat-6. Infection and Immunity 69:2773-2778.

15. Ravn, P., A. Demissie, T. Eguale, H. Wondwosson, D. Lein, H. Amoudy, A. S. Mustafa, A. K. Jensen, A. Holm, I. Rosenkrands, F. Oftung, J. Olobo, C. F. von-Reyn, and P. Andersen. 1999. Human T cell responses to the ESAT-6 antigen from Mycobacterium tuberculosis. J. Infect. Dis. 179:637-645.
16. Skeiky, Y. A., M. R. Alderson, P. J. Ovendale, J. A. Guderian, L. Brandt, D. C. Dillon, A. Campos-Neto, Y. Lobet, W. Dalemans, I. M. Orme, and S. G. Reed. 2004. Differential immune responses and protective efficacy induced by components of a tuberculosis polyprotein vaccine, Mtb72F, delivered as naked DNA or recombinant protein. J Immunol 172:7618-7628.
17. Stockinger, B., C. Bourgeois, and G. Kassiotis. 2006. CD4+ memory T cells: functional differentiation and homeostasis. Immunol Rev 211:39-48.
18. Weinreich Olsen, A., L. A. van Pinxteren, L. Meng Okkels, P. Birk Rasmussen, and P. Andersen. 2001. Protection of mice with a tuberculosis subunit vaccine based on a fusion protein of antigen 85b and esat-6. Infect Immun 69:2773-2778.
19. Wu, C. Y., J. R. Kirman, M. J. Rotte, D. F. Davey, S. P. Perfetto, E. G. Rhee, B. L. Freidag, B. J. Hill, D. C. Douek, and R. A. Seder. 2002. Distinct lineages of T(H)1 cells have differential capacities for memory cell generation in vivo. Nature immunology 3:852-858.
20. US FDA. 1995. Guidance for industry: Estimating the Maximum Safe Starting Dose in initial clinical trials for therapeutics in adult healthy volunteers. U.S. Department of Health and Human Services, Food and Drug Administration, Center for Drug Evaluation and Research.
21. Leroux-Roels I, Leroux-Roels G, Ofori-Anyinam O et al. Safety and immunogenicity of the Mtb72f/AS02A tuberculosis vaccine in PPD-negative Belgian adults. Medical and Health in the Tropics. Marseille, France, 11-15 Sep. 2005 (Abstract 0-036).

All publications listed in this specification are incorporated herein by reference. While the invention has been described with reference to particular embodiments, it will be appreciated that modifications can be made without departing from the spirit of the invention. Such modifications are intended to fall within the scope of the appended claims.

SEQUENCE LISTING

```
<160> NUMBER OF SEQ ID NOS: 11

<210> SEQ ID NO 1
<211> LENGTH: 11
<212> TYPE: PRT
<213> ORGANISM: Unknown
<220> FEATURE:
<223> OTHER INFORMATION: polycationic peptide

<400> SEQUENCE: 1

Lys Leu Lys Leu Leu Leu Leu Leu Lys Leu Lys
1               5                   10


<210> SEQ ID NO 2
<211> LENGTH: 26
<212> TYPE: DNA
<213> ORGANISM: Unknown
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: n represents inosine
<220> FEATURE:
<221> NAME/KEY: misc_feature
<222> LOCATION: (3)..(3)
<223> OTHER INFORMATION: n represents inosine
<220> FEATURE:
<221> NAME/KEY: misc_feature
<222> LOCATION: (5)..(5)
<223> OTHER INFORMATION: n represents inosine
<220> FEATURE:
<221> NAME/KEY: misc_feature
<222> LOCATION: (7)..(7)
<223> OTHER INFORMATION: n represents inosine
<220> FEATURE:
<221> NAME/KEY: misc_feature
<222> LOCATION: (9)..(9)
<223> OTHER INFORMATION: n represents inosine
<220> FEATURE:
<221> NAME/KEY: misc_feature
<222> LOCATION: (11)..(11)
<223> OTHER INFORMATION: n represents inosine
<220> FEATURE:
<221> NAME/KEY: misc_feature
<222> LOCATION: (13)..(13)
```

<223> OTHER INFORMATION: n represents inosine
<220> FEATURE:
<221> NAME/KEY: misc_feature
<222> LOCATION: (15)..(15)
<223> OTHER INFORMATION: n represents inosine
<220> FEATURE:
<221> NAME/KEY: misc_feature
<222> LOCATION: (17)..(17)
<223> OTHER INFORMATION: n represents inosine
<220> FEATURE:
<221> NAME/KEY: misc_feature
<222> LOCATION: (19)..(19)
<223> OTHER INFORMATION: n represents inosine
<220> FEATURE:
<221> NAME/KEY: misc_feature
<222> LOCATION: (21)..(21)
<223> OTHER INFORMATION: n represents inosine
<220> FEATURE:
<221> NAME/KEY: misc_feature
<222> LOCATION: (23)..(23)
<223> OTHER INFORMATION: n represents inosine
<220> FEATURE:
<221> NAME/KEY: misc_feature
<222> LOCATION: (25)..(25)
<223> OTHER INFORMATION: n represents inosine

<400> SEQUENCE: 2 ncncncncnc ncncncncnc ncncnc 26

<210> SEQ ID NO 3
<211> LENGTH: 338
<212> TYPE: PRT
<213> ORGANISM: Mycobacterium tuberculosis

<400> SEQUENCE: 3

Met Gln Leu Val Asp Arg Val Arg Gly Ala Val Thr Gly Met Ser Arg
1 5 10 15

Arg Leu Val Val Gly Ala Val Gly Ala Ala Leu Val Ser Gly Leu Val
20 25 30

Gly Ala Val Gly Gly Thr Ala Thr Ala Gly Ala Phe Ser Arg Pro Gly
35 40 45

Leu Pro Val Glu Tyr Leu Gln Val Pro Ser Pro Ser Met Gly Arg Asp
50 55 60

Ile Lys Val Gln Phe Gln Ser Gly Gly Ala Asn Ser Pro Ala Leu Tyr
65 70 75 80

Leu Leu Asp Gly Leu Arg Ala Gln Asp Asp Phe Ser Gly Trp Asp Ile
85 90 95

Asn Thr Pro Ala Phe Glu Trp Tyr Asp Gln Ser Gly Leu Ser Val Val
100 105 110

Met Pro Val Gly Gly Gln Ser Ser Phe Tyr Ser Asp Trp Tyr Gln Pro
115 120 125

Ala Cys Gly Lys Ala Gly Cys Gln Thr Tyr Lys Trp Glu Thr Phe Leu
130 135 140

Thr Ser Glu Leu Pro Gly Trp Leu Gln Ala Asn Arg His Val Lys Pro
145 150 155 160

Thr Gly Ser Ala Val Val Gly Leu Ser Met Ala Ala Ser Ser Ala Leu
165 170 175

Thr Leu Ala Ile Tyr His Pro Gln Gln Phe Val Tyr Ala Gly Ala Met
180 185 190

Ser Gly Leu Leu Asp Pro Ser Gln Ala Met Gly Pro Thr Leu Ile Gly
195 200 205

Leu Ala Met Gly Asp Ala Gly Gly Tyr Lys Ala Ser Asp Met Trp Gly
210 215 220

```
Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
        275                 280                 285

Ala Gly Gly Gly His Asn Gly Val Phe Asp Phe Pro Asp Ser Gly Thr
    290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala


<210> SEQ ID NO 4
<211> LENGTH: 325
<212> TYPE: PRT
<213> ORGANISM: Mycobacterium tuberculosis

<400> SEQUENCE: 4

Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
    130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255
```

```
Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
    290                 295                 300

Glu Tyr Trp Gly Ala Gln Leu Asn Ala Met Lys Gly Asp Leu Gln Ser
305                 310                 315                 320

Ser Leu Gly Ala Gly
                325


<210> SEQ ID NO 5
<211> LENGTH: 340
<212> TYPE: PRT
<213> ORGANISM: Mycobacterium tuberculosis

<400> SEQUENCE: 5

Met Thr Phe Phe Glu Gln Val Arg Arg Leu Arg Ser Ala Ala Thr Thr
1               5                   10                  15

Leu Pro Arg Arg Leu Ala Ile Ala Ala Met Gly Ala Val Leu Val Tyr
            20                  25                  30

Gly Leu Val Gly Thr Phe Gly Gly Pro Ala Thr Ala Gly Ala Phe Ser
        35                  40                  45

Arg Pro Gly Leu Pro Val Glu Tyr Leu Gln Val Pro Ser Ala Ser Met
    50                  55                  60

Gly Arg Asp Ile Lys Val Gln Phe Gln Gly Gly Gly Pro His Ala Val
65                  70                  75                  80

Tyr Leu Leu Asp Gly Leu Arg Ala Gln Asp Asp Tyr Asn Gly Trp Asp
                85                  90                  95

Ile Asn Thr Pro Ala Phe Glu Glu Tyr Tyr Gln Ser Gly Leu Ser Val
            100                 105                 110

Ile Met Pro Val Gly Gly Gln Ser Ser Phe Tyr Thr Asp Trp Tyr Gln
        115                 120                 125

Pro Ser Gln Ser Asn Gly Gln Asn Tyr Thr Tyr Lys Trp Glu Thr Phe
    130                 135                 140

Leu Thr Arg Glu Met Pro Ala Trp Leu Gln Ala Asn Lys Gly Val Ser
145                 150                 155                 160

Pro Thr Gly Asn Ala Ala Val Gly Leu Ser Met Ser Gly Gly Ser Ala
                165                 170                 175

Leu Ile Leu Ala Ala Tyr Tyr Pro Gln Gln Phe Pro Tyr Ala Ala Ser
            180                 185                 190

Leu Ser Gly Phe Leu Asn Pro Ser Glu Gly Trp Trp Pro Thr Leu Ile
        195                 200                 205

Gly Leu Ala Met Asn Asp Ser Gly Gly Tyr Asn Ala Asn Ser Met Trp
    210                 215                 220

Gly Pro Ser Ser Asp Pro Ala Trp Lys Arg Asn Asp Pro Met Val Gln
225                 230                 235                 240

Ile Pro Arg Leu Val Ala Asn Asn Thr Arg Ile Trp Val Tyr Cys Gly
                245                 250                 255

Asn Gly Thr Pro Ser Asp Leu Gly Gly Asp Asn Ile Pro Ala Lys Phe
            260                 265                 270

Leu Glu Gly Leu Thr Leu Arg Thr Asn Gln Thr Phe Arg Asp Thr Tyr
        275                 280                 285

Ala Ala Asp Gly Gly Arg Asn Gly Val Phe Asn Phe Pro Pro Asn Gly
```

```
    290                 295                 300

Thr His Ser Trp Pro Tyr Trp Asn Glu Gln Leu Val Ala Met Lys Ala
305                 310                 315                 320

Asp Ile Gln His Val Leu Asn Gly Ala Thr Pro Pro Ala Ala Pro Ala
                325                 330                 335

Ala Pro Ala Ala
            340


<210> SEQ ID NO 6
<211> LENGTH: 96
<212> TYPE: PRT
<213> ORGANISM: Mycobacterium tuberculosis

<400> SEQUENCE: 6

Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95


<210> SEQ ID NO 7
<211> LENGTH: 11
<212> TYPE: PRT
<213> ORGANISM: Unknown
<220> FEATURE:
<223> OTHER INFORMATION: polycationic peptide

<400> SEQUENCE: 7

Arg Leu Arg Leu Leu Leu Leu Leu Arg Leu Arg
1               5                   10


<210> SEQ ID NO 8
<211> LENGTH: 11
<212> TYPE: PRT
<213> ORGANISM: Unknown
<220> FEATURE:
<223> OTHER INFORMATION: polycationic peptide

<400> SEQUENCE: 8

Arg Leu Lys Leu Leu Leu Leu Leu Lys Leu Arg
1               5                   10


<210> SEQ ID NO 9
<211> LENGTH: 11
<212> TYPE: PRT
<213> ORGANISM: Unknown
<220> FEATURE:
<223> OTHER INFORMATION: polycationic peptide

<400> SEQUENCE: 9

Lys Phe Lys Phe Phe Phe Phe Phe Lys Phe Lys
1               5                   10


<210> SEQ ID NO 10
<211> LENGTH: 11
```

-continued

```
<212> TYPE: PRT
<213> ORGANISM: Unknown
<220> FEATURE:
<223> OTHER INFORMATION: polycationic peptide

<400> SEQUENCE: 10

Lys Trp Lys Trp Trp Trp Trp Trp Lys Trp Lys
1               5                   10


<210> SEQ ID NO 11
<211> LENGTH: 11
<212> TYPE: PRT
<213> ORGANISM: Unknown
<220> FEATURE:
<223> OTHER INFORMATION: polycationic peptide

<400> SEQUENCE: 11

Lys Val Lys Val Val Val Val Val Lys Val Lys
1               5                   10
```

The invention claimed is:

1. A method of inducing an immune response against M. tuberculosis in a [mammal] *human*, the method comprising introducing into said [mammal] *human* an immunogenic composition comprising a TB10.4 protein, an Ag85-complex protein, and an adjuvant comprising at least one polycationic peptide and at least one polydeoxyinosinic-deoxycytidylic acid, wherein the total amount of the TB10.4 protein and the Ag85-complex protein is [less than about 1 μg] *about 5 μg to about 25 μg*.

2. The method according to claim 1, wherein the TB10.4 protein and the Ag85-complex protein are present as a fusion protein.

3. The method according to claim 2, wherein the fusion protein is present in an amount equal to about [0.5 μg] *10 μg to about 25 μg*.

4. The method according to claim [2] *3*, wherein the fusion protein is present in an amount equal to about [0.1 μg] *15 μg*.

5. The method according to claim 1, wherein the Ag85-complex protein is an Ag85B protein.

6. The method according to claim 1, wherein the at least one oligonucleotide is a TLR9 agonist.

7. The method according to claim 1, wherein the adjuvant is a mixture of [peptide] NH2-KLKLLLLLKLK-COOH (SEQ ID NO: 1) and [oligonucleotide] 5'-ICI CIC ICI CIC ICI CIC ICI CIC IC-3' (SEQ ID NO:2).

[8. The method according to claim 1, wherein said mammal is a human.]

9. A method of inducing protection against M. tuberculosis in a [mammal] *human*, the method comprising introducing into said [mammal] *human* an immunogenic composition comprising a TB10.4 protein, an Ag85-complex protein, and an adjuvant comprising at least one polycationic peptide and at least oligonucleotide-5'-ICI CIC ICI CIC ICI CIC ICI CIC IC-3' (SEQ ID NO:2), wherein the total amount of the TB10.4 protein and the Ag85-complex protein is [less than about 1 μg] *about 5 μg to about 25 μg*.

10. The method according to claim 9, wherein the TB10.4 protein and the Ag85-complex protein are present as a fusion protein.

11. The method according to claim 10, wherein the fusion protein is present in an amount equal to about [0.5 μg] *10 μg to about 25 μg*.

12. The method according to claim [10] *11*, wherein the fusion protein is present in an amount equal to about [0.1 μg] *15 μg*.

13. The method according to claim 9, wherein the Ag85-complex protein is an Ag85B protein.

14. The method according to claim 9, wherein the at least one oligonucleotide is a TLR9 agonist.

15. The method according to claim 9, wherein the adjuvant is a mixture of peptide $NH_2$-KLKLLLLLKLK-COOH (SEQ ID NO:1) and oligonucleotide 5'-ICI CIC ICI CIC ICI CIC ICI CIC IC-3' (SEQ ID NO:2).

[16. The method according to claim 9, wherein said mammal is a human.]

17. A method of inducing an immune response against M. tuberculosis in a [mammal] *human*, the method comprising introducing into said [mammal] *human* an immunogenic composition comprising a TB10.4 protein, an Ag85-complex protein, and an adjuvant comprising at least one polycationic peptide and at least one polydeoxyinosinic-deoxycytidylic acid, wherein the total amount of the TB10.4 protein and the Ag85-complex protein [ranges from 0.1 μg to 1 μg] *is about 15 μg*.

18. The method according to claim 17, wherein the TB10.4 protein and the Ag85-complex protein are present as a fusion protein.

[19. The method according to claim 18, wherein the fusion protein is present in an amount equal to about 0.5 μg.]

20. The method according to claim 17, wherein the adjuvant is a mixture of [peptide] NH2-KLKLLLLLKLK-COOH (SEQ ID NO: 1) and [oligonucleotide] 5'-ICI CIC ICI CIC ICI CIC ICI CIC IC-3' (SEQ ID NO:2).

*21. The method according to claim 1, wherein the total amount of the TB10.4 protein and the Ag85-complex protein is about 10 μg to about 25 μg.*

*22. The method according to claim 21, wherein the total amount of the TB10.4 protein and the Ag85-complex protein is about 15 μg.*

*23. The method according to claim 9, wherein the total amount of the TB10.4 protein and the Ag85-complex protein is about 15 μg.*

* * * * *